(12) United States Patent
Ji

(10) Patent No.: US 7,224,448 B2
(45) Date of Patent: May 29, 2007

(54) APPARATUS AND METHODS FOR EVALUATING AN OPTICAL PROPERTY OF A LIQUID SAMPLE

(75) Inventor: Zhenghua Ji, Wilmington, DE (US)

(73) Assignee: Agilent Technologies, Inc., Santa Clara, CA (US)

(*) Notice: Subject to any disclaimer, the term of this patent is extended or adjusted under 35 U.S.C. 154(b) by 417 days.

(21) Appl. No.: 10/989,957

(22) Filed: Nov. 16, 2004

(65) Prior Publication Data
US 2006/0103849 A1  May 18, 2006

(51) Int. Cl.
*G01N 21/01* (2006.01)

(52) U.S. Cl. .................. 356/244; 356/246; 356/436; 73/863.32; 73/864.72

(58) Field of Classification Search .......... 73/863.2, 73/864.72; 356/440, 441, 442, 246, 436, 356/244; 250/428, 576
See application file for complete search history.

(56) References Cited

U.S. PATENT DOCUMENTS

| | | | |
|---|---|---|---|
| 3,720,354 A | 3/1973 | Drummond et al. | |
| 3,828,987 A | 8/1974 | Drummond et al. | |
| 4,547,075 A * | 10/1985 | Fei .............................. | 356/440 |
| 4,643,580 A | 2/1987 | Gross et al. | |
| 4,910,402 A | 3/1990 | McMillan | |
| 4,991,958 A | 2/1991 | Garner | |
| 5,416,879 A | 5/1995 | Liu | |
| 5,444,807 A | 8/1995 | Liu | |
| 5,460,782 A | 10/1995 | Coleman et al. | |
| 5,674,457 A | 10/1997 | Williamsson et al. | |
| 5,815,258 A | 9/1998 | Nakanishi | |
| 5,824,269 A * | 10/1998 | Kosaka et al. ............... | 422/73 |
| 5,844,686 A | 12/1998 | Treptow et al. | |
| 6,104,485 A | 8/2000 | Wang et al. | |
| 6,214,626 B1 | 4/2001 | Meller et al. | |
| 6,249,345 B1 * | 6/2001 | Kraack et al. .............. | 356/246 |
| 6,396,584 B1 | 5/2002 | Taguchi et al. | |
| 6,541,266 B2 | 4/2003 | Modzelewski et al. | |
| 6,628,382 B2 | 9/2003 | Robertson | |
| 6,809,826 B2 * | 10/2004 | Robertson ................... | 356/440 |
| 2002/0058342 A1 | 5/2002 | Lilja et al. | |
| 2002/0136667 A1 | 9/2002 | Subramanian et al. | |
| 2002/0140931 A1 | 10/2002 | Robertson | |
| 2002/0154299 A1 | 10/2002 | Robertson | |
| 2005/0094127 A1 * | 5/2005 | O'mahony et al. .......... | 356/39 |
| 2005/0181519 A1 * | 8/2005 | Karg et al. .................. | 436/180 |

FOREIGN PATENT DOCUMENTS

EP  0158948  4/1985

* cited by examiner

*Primary Examiner*—Gregory J. Toatley, Jr.
*Assistant Examiner*—Harish Panth

(57) ABSTRACT

An apparatus for acquiring and holding minimum size liquid samples with predetermined pathlength and methods using the same.

26 Claims, 5 Drawing Sheets

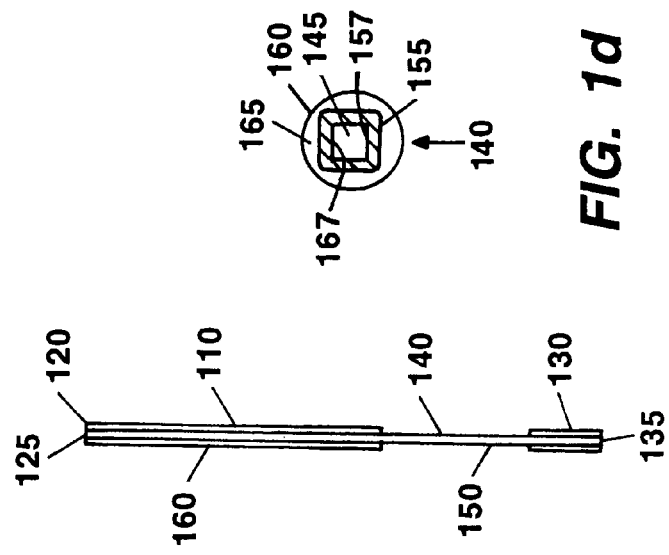
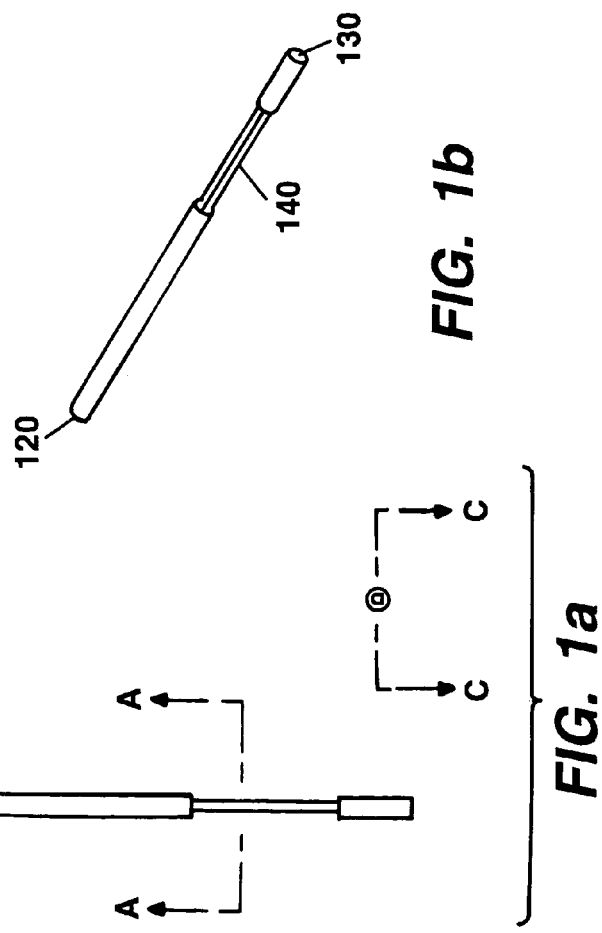

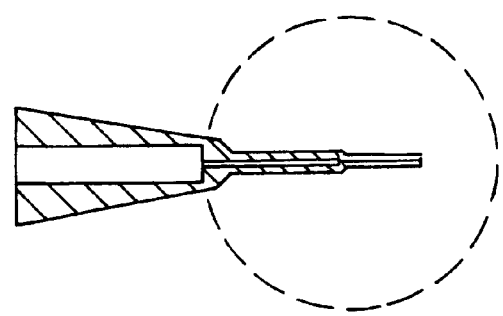
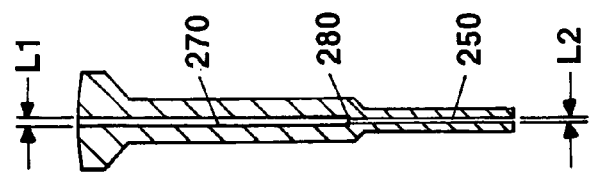
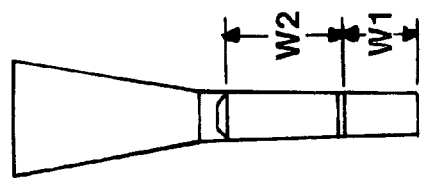
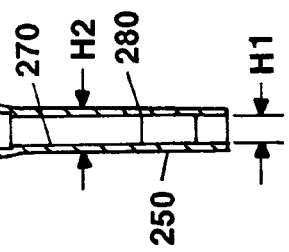
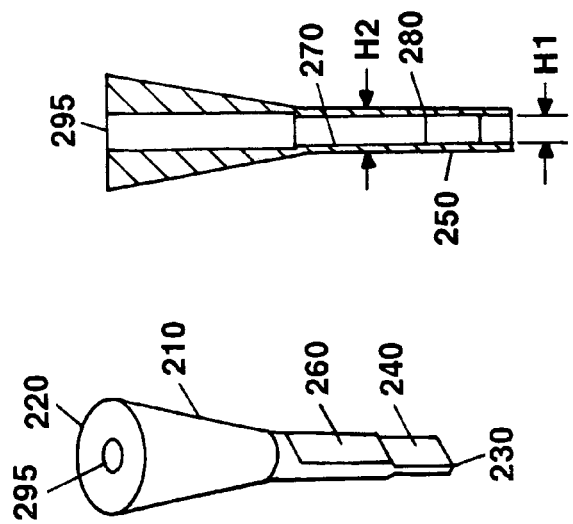
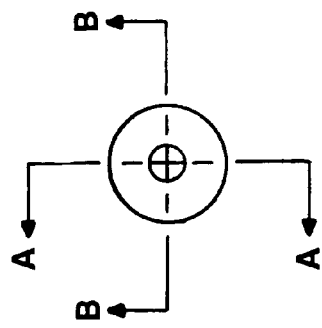

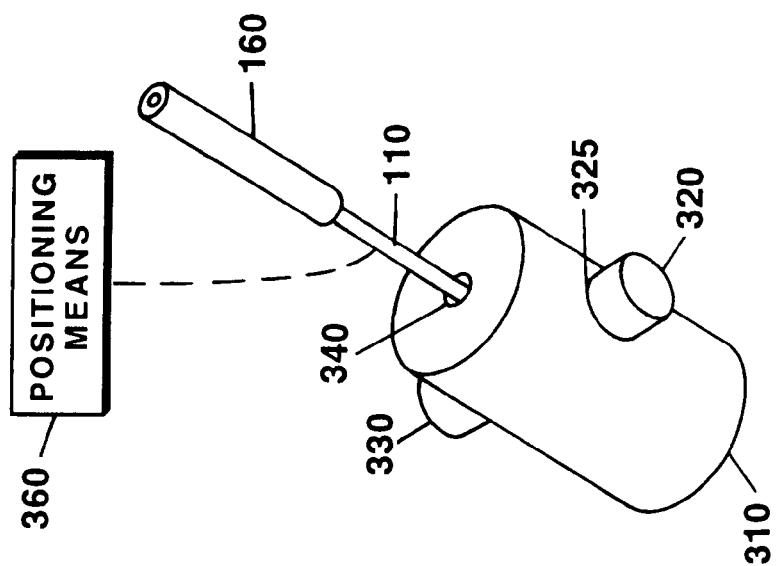
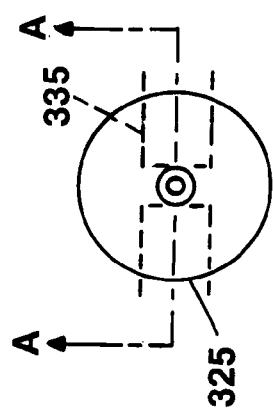
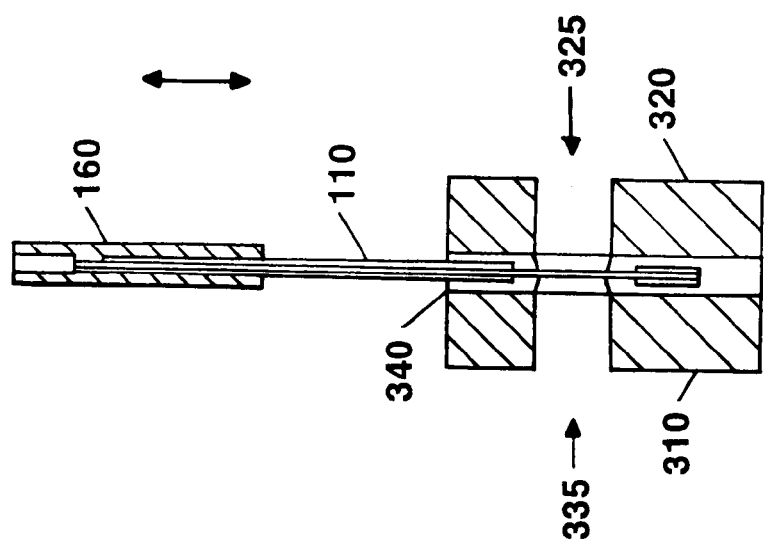

APPARATUS AND METHODS FOR EVALUATING AN OPTICAL PROPERTY OF A LIQUID SAMPLE

BACKGROUND OF THE INVENTION

There are many use environments, the fields of medical research and pharmaceutical development being examples, where it is necessary to accurately acquire fluid samples with volumes that may be as small as a few nanoliters. In these same fields, it is also often desirable to measure optical characteristics of the acquired fluid samples. Such optical characteristics include, for example, the ability of a sample to absorb light.

For instance, UV-Visible Spectrophotometry may be used to characterize the chemical composition of a liquid sample (in solution or suspension phase) using the absorbed spectra of the sample. The light absorbance of a sample depends on the pathlength L of light passing through the sample, as well as on the concentration of light absorbers (e.g., biomolecules, cells, etc) in a sample solution and the wavelength (λ) of light being used to characterize the sample. The wavelengths of UV-Visible light span from 200 nm to 800 nm, while ultraviolet wavelengths range from 200 to 400 nm.

UV-Visible spectrophotometry provides a convenient analysis technique to determine the concentration, purity, and integrity of a biological sample without requiring additional sample preparation other than acquiring a sample. UV-Visible Spectrophotometry measurements depend on the light source (UV lamp), the sample and sampling technique. Most biological samples absorb electromagnetic radiation at wavelengths ranging from 200 nm to 800 nm, mostly 230, 260 and 280 nm. For a DNA or RNA sample in aqueous phase, one unit of absorbance 1 Å measured at a λ 260 nm and a pathlength of 10 mm is equal to 50/(40) ng/µl concentration.

Most biological samples are highly concentrated for downstream processing (such as microarray spotting or protein sample preparation for mass spectrometers). The absorbance of such samples can be above the saturation limit for typical spectrophotometers if the pathlength is about 10 mm. While the sample concentration range can be extended by diluting the sample, diluting sample requires additional laboratory work and can result in errors. Other approaches are needed to extend the sample concentration range that can be evaluated by the instrument.

Sampling techniques used in conventional UV-Visible Spectrophotometers include utilizing a cuvette with an optical window and fixed optical pathlength that holds a sample in a semi-closed way, direct measurement of liquid sample in a sample container (e.g., a well) along with a real-time pathlength measurement, and using a cuvetteless sample held in semi-free space between optical fibers which define a light path from a light source to a detector.

The cuvette-based sampling technique is widely used in conventional UV-Visible spectrophotometers. Generally, a sample is pipetted into a cuvette that has either a 10 mm or 2 mm path length. This technique is very limited for most biological samples since cuvettes typically used generally require a minimum 10 µl sample, which is problematic for valuable biological samples which may be present in limiting quantities, such as samples of protein or nucleic acids. A cuvette made of quartz or silica is expensive so it is typically reused after cleaning and drying. Further, adding 10 µl of sample with a pipette into a cuvette sometimes produces an air-bubble interface in the light path that can cause measurement error or void measurements. Additionally, a pathlength of 2 mm or 10 mm limits the sample concentration that may be measured to 1000 ng/µl for DNA/RNA sample due to the limited dynamic range of absorbance of most spectrophotometers.

Direct UV-Visible spectrophotometry measurement of liquid samples also suffers from limitations, such as the need to determine pathlength and adjust sample concentration. Pathlength depends on the sample well dimensions and sample volume. The determination of pathlength requires use of instruments such as level detectors or position sensors. For a pathlength ranging from 2 mm to 10 mm or above, the workable range of sample concentration for a spectrophotometer measurement becomes limited. For an example, for a DNA sample, if the pathlength is 10 mm, one unit of absorbance is equal to 50 ng/ul concentration (OD), and the upper limit of detection is typically 250 ng/µl if the upper limit absorbance of the spectrophotometer is 5. In this case, sample dilution is required for a sample concentration greater than 250 ng/µl. Sample dilution for multiple well plate measurements can be a complex laboratory operation.

Cuvetteless sampling also suffers from drawbacks. For example, in cuvetteless sampling, typically a narrow beam of light is directed to a sample stage that consists of a 1-2 µl liquid droplet suspended between two multi-mode optical fibers, one source-side fiber which provides light from a light source to the droplet and a detection-side fiber that guides light from the droplet to appropriate detection optics. The close proximity between the source-side and detection-side fibers allows enough of the light cone emanating from the source-side fiber to be collected by the detection-side fiber after passing through a liquid sample.

Cuvetteless instruments typically require a clamping surface that can be wetted with sample to avoid an air-bubble interface. Carry-over contamination is not completely removed with a simple wiping-off of the clamping surface. Adding a small amount of sample (1 µl) to the center of the clamping surface is also a complicated lab technique.

In summary, existing sampling techniques used in the conventional UV-Visible Spectrophotometers generally require too much sample, provide insufficient confidence in the sample application technique, may result in carry-over contamination, and may require pathlength determination and/or dilution of sample, over a range of solution concentrations.

SUMMARY OF THE INVENTION

In one aspect, the invention provides an apparatus for acquiring and holding a small volume of a liquid sample (e.g., less than about 5 µl, or about 2 µl or less) whose optical properties may be detected, monitored and/or quantitated without determining an optical pathlength for the sample and/or apparatus in which the sample is placed.

In one embodiment, the apparatus includes a body having a first opening located at a first end, a second opening located at a second end, two planar inner surfaces, and two planar outer surfaces, where the two planar outer surfaces are substantially parallel to the two planar inner surfaces.

An inner space within the body connects the first opening and the second opening and provides a passage from the first opening to the second opening. The two inner surfaces form two sides of a portion of the passage. In one aspect, the two surfaces are parallel for at least a portion of their length. In another aspect, the passage defined by the space between the two parallel portions of the body constitutes a measurement area of the device. The passageway may be square, rectangular or polygonal. In one aspect, the pathlength of a light passing through a measurement area of the apparatus is predetermined. In another aspect, the pathlength is less than about 10 mm, less than about 5 mm, less than about 2 mm, or about 1 mm or less.

At least a portion of the body is made of material semi-transparent or transparent to electromagnetic radiation in some wavelength range that is detectable by a detection system being used. In one aspect, at least one of the first opening and second opening have a dimension sufficiently small to enable a liquid to enter and be held within the passage by capillary forces sufficient to hold the liquid sample against opposing forces such as gravity or other forces such as small pressure changes or gentle thermal expansion.

In another aspect, the invention provides an adaptor for providing a substantially gastight connection to a pipette/pipettor (e.g., such as a Pipetman®, a Gilson®, Rainin®, Eppendorf® or Finnipipette® pipette) or a fluid-dispensing device. In one aspect, the adaptor is configured in the shape of a pipette tip.

In another embodiment, the invention provides a holder comprising a housing capable of receiving the apparatus body. In one aspect, the holder housing has two openings that are substantially aligned to define a light transmission path for electromagnetic radiation when the hollow body is held in the housing.

BRIEF DESCRIPTION OF THE DRAWINGS

For a better understanding of the present invention, reference is made to the accompanying drawings and detailed description and its scope will be pointed out in the appended claims.

FIGS. 1a, 1b, 1c and 1d are views of a schematic representation of an embodiment of the apparatus of this invention;

FIGS. 3a, 3b, 3c, 3d and 3e are views of a schematic representation of another embodiment of the apparatus of this invention;

FIGS. 4a, 4b and 4c are views of a schematic representation of yet another embodiment of the apparatus of this invention.

DETAILED DESCRIPTION OF THE INVENTION

Figure 2C:
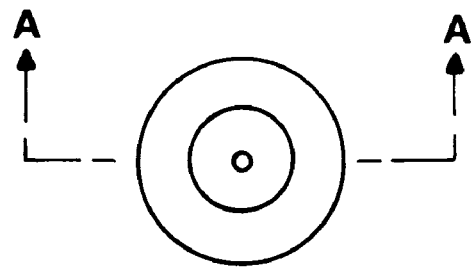
FIGS. 2a, 2b and 2c are views of a schematic representation of an embodiment of an adaptor of this invention.

Before describing the present invention in detail, it is to be understood that this invention is not limited to specific apparatuses, method steps, or equipment, as such may vary. It is also to be understood that the terminology used herein is for the purpose of describing particular embodiments only, and is not intended to be limiting. Methods described herein may be carried out in any order of the recited steps that is logically possible. Furthermore, where a range of values is provided, it is understood that every intervening value, between the upper and lower limit of that range and any other stated or intervening value in that stated range is encompassed within the invention. Also, it is contemplated that any optional feature of the inventive embodiments and aspects described herein may be set forth and claimed independently, or in combination with any one or more of the features described herein, or may be specifically excluded.

Unless defined otherwise below, all technical and scientific terms used herein have the same meaning as commonly understood by one of ordinary skill in the art to which this invention belongs. Still, certain terms are defined herein for the sake of clarity.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed. All publications mentioned herein are incorporated herein by reference to disclose and describe the methods and/or materials in connection with which the publications are cited.

It must be noted that, as used in this specification and the appended claims, the singular forms "a", "an" and "the" include plural referents unless the context clearly dictates otherwise. Thus, for example, reference to "a biopolymer" includes more than one biopolymer, and the like.

It will also be appreciated that throughout the present application, that words such as "upper", "lower" are used in a relative sense only.

The following definitions are provided for specific terms that are used in the following written description.

A "biopolymer" is a polymer of one or more types of repeating units. Biopolymers are typically found in biological systems and particularly include polysaccharides (such as carbohydrates), peptides (which term is used to include polypeptides and proteins, such as antibodies or antigen-binding proteins), glycans, proteoglycans, lipids, sphingolipids, and polynucleotides as well as their analogs such as those compounds composed of or containing amino acid analogs or non-amino acid groups, or nucleotide analogs or non-nucleotide groups. Biopolymers may be heterogeneous in backbone composition thereby containing any possible combination of polymer units linked together such as peptide-nucleic acids (which have amino acids linked to nucleic acids and have enhanced stability).

Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. Biopolymers include DNA (including cDNA), RNA, oligonucleotides, PNA, LNA and other polynucleotides as described in U.S. Pat. No. 5,948,902 and references cited therein, regardless of the source.

"Communicating information" refers to transmitting the data representing that information as signals (e.g., electrical, optical, radio, magnetic, etc) over a suitable communication channel (e.g., a private or public network).

As used herein, a component of a system which is "in communication with" or "communicates with" another component of a system receives input from that component and/or provides an output to that component to implement a system function. A component which is "in communication with" or which "communicates with" another component may be, but is not necessarily, physically connected to the other component. For example, there may be a structural, functional, mechanical, optical, or fluidic relationship between two or more components or elements, or some combination thereof. As such, the fact that one component is said to communicate with a second component is not intended to exclude the possibility that additional components may be present between, and/or operatively associated or engaged with, the first and second components.

The term "assessing" and "evaluating" are used interchangeably to refer to any form of measurement, and includes determining if an element is present or not. The terms "determining," "measuring," and "assessing," and "assaying" are used interchangeably and include both quantitative and qualitative determinations. Assessing may be relative or absolute. "Assessing the presence of" includes determining the amount of something present, as well as determining whether it is present or absent.

The term "using" has its conventional meaning, and, as such, means employing, e.g. putting into service, a method or composition to attain an end.

An apparatus for holding small volume liquid samples with a predetermined pathlength is described hereinbelow.

In one embodiment, the apparatus includes a body having a first opening located at a first end, a second opening located at a second end, two planar inner surfaces, and two planar outer surfaces, where the two planar outer surfaces are substantially parallel to the two planar inner surfaces (such that each inner surface has a corresponding planar outer surface to which it is substantially parallel).

The body connects the first opening and the second opening and comprises a passage from the first opening to the second opening whose walls are formed by the inner surfaces of the hollow body. In one aspect, the two inner surfaces are parallel for at least a portion of their length, forming a measurement area that is polygonal in cross-section (e.g., square or rectangular). The measurement area of the device comprises a portion of a first inner surface and its corresponding outer surface, a portion of a second inner surface and its corresponding outer surface, and a passage between them for holding a liquid sample by capillary action. In one aspect, the distance from a first inner surface to a second parallel inner surface is less than about 10 mm, less than about 5 mm, less than about 3 mm, 2 mm or less. The distance, in certain aspects, ranges from about 0.1 to 2 mm.

An embodiment of the apparatus 110 of this invention is shown in FIGS. 1a, 1b, 1c and 1d. In the embodiment shown in FIGS. 1a-1d, the apparatus comprises a body 110 that has two open ends 120, 130 with corresponding openings 125, 135. The body 110 of the embodiment shown in FIGS. 1a-1d has a square shaped flow channel 150, having at least planar inner 157, 167 and outer surfaces 155, 165, where the planar outer surfaces 155, 165 are substantially parallel to the planar inner surfaces 157, 167.

The body 110 of the embodiment shown in FIGS. 1a-1d comprises a dimension sufficiently small to hold a liquid sample within the passageway by capillary action, despite opposing forces such as gravity.

In one aspect, at least one inner surface 157, 167 and its corresponding parallel outer surface 155, 165 is at least partially transparent. In another aspect, at least two inner surfaces 157, 167 and their corresponding parallel outer surfaces 155, 165 are at least partially transparent. An "at least partially transparent" material, as used herein, refers to a material that transmits sufficient light that may be detected by a detection device in an optical instrument (e.g., such as a spectrophotometer). In one aspect, an "at least partially transparent material has at least about 50% transmittance of electromagnetic radiation.

In a further aspect, first 157 and second 167 at least partially transparent inner surfaces are sufficiently parallel to each other and dimensioned to hold a liquid sample between them in a measurement area by capillary action, such that light from a light source may pass through the first inner surface 157 (and its corresponding outer surface 155), the liquid sample, and the second inner surface 167 (and its corresponding outer surface 165).

Materials used to form the at least partially transparent portion(s) of the body may vary and may include any at least partially transparent material, for example, a polymeric material such as polyimide, polycarbonate, polystyrene, polyolefin, fluoropolymer, polyester, a nonaromatic hydrocarbon, polyvinylidene chloride, polyhalocarbon, such as polycholortrifluoroethylene. Polyolefins may include polyethylenes, polymethylpentenes and polypropylenes, and fluoropolymers may include polyvinyl fluorides. Other materials glass, quartz, silica, silicon rubber, such as crosslinked dimethyldisiloxane, or materials used in optical crystals, such as sapphire or garnet (e.g., undoped Yttrium Aluminum Garnet). In certain aspects, the material transmits light with a range of about 200-1100 nm, from about 180-1000 nm, and/or transmits light of a wavelength greater than about 900 nm. The apparatus of this invention can be manufactured by casting or molding or other methods routine in the art.

In certain aspects, materials and dimensions are selected to ensure that a measured signal relating to a sample within the measurement area of the body remains within the limit of the linear range for measurements by a particular detection device with which the apparatus of this invention is used (e.g., such as a spectrophotometer, photometer, spectrofluorometer, and the like).

In one aspect, the body comprises an outer coating or clad 160. In certain aspects, the outer coating reduces stray light (light other than from a light source being using by the optical detector) during optical measurement. In one aspect, the coating comprises a UV absorber.

However, in another aspect, at least a portion of the body is not coated to provide an optical window or aperture 140. In one aspect, a clad is stripped at one section to form the optical window 160. In another aspect, to reduce surface scattering during the optical measurement, the outer surface of the aperture window is smooth. Portions of the surface may be removed to create the desired smooth surface (e.g., by laser machining) or materials may be added to create a smooth surface (e.g., an at least partially transparent coating may be provided).

In embodiments in which the optical window-containing portion of the body is directly dipped into a liquid sample, a portion of the surface area of the body 110 may, in one embodiment, be coated by a hydrophobic coating to eliminate/prevent any liquid sample residue remaining on the outer surface of the body 110. In one aspect, the coating is less than about 1 µm in thickness. In another aspect, the coating is transparent or semi-transparent to electromagnetic radiation. An exemplary embodiment of a hydrophobic coating material comprises a siloxane, for example, the coating may be polydimethylsiloxane silicon rubber, PTFE (e.g., Teflon), a polyacrylate, and the like but this invention is not limited to only these exemplary embodiments.

In one aspect, the passage connecting the first and second openings comprises a channel. Channel dimensions may range from about 50 µm×50 µm to about 2 mm×2 mm, and in one aspect, the passage holds a minimum channel volume of about 25 nl. In certain aspects, the passage comprises varying channel dimensions at one or more sections through the length of the body. However, in one aspect, the channel dimensions within the measurement area do not vary.

In some embodiments, the length of the body 110 ranges from about 2 mm to about 100 mm. In one embodiment, an optical window 140 is positioned approximately 0-10 mm above the bottom end 130, and has an aperture width ranging from about 1 mm to about 10 mm. In one embodiment, but not a limitation of this invention, the outer coating 160, which covers a portion of the body excluding the optical window, is round, with diameter ranging from about 0.3 mm to approximately 3 mm. The outer coating 160 can be, but is not limited to, a polymeric material such as polyamide. The outer coating 160 can also be an at least partially UV transparent material.

In one aspect, at least a portion of the body 110 is comprised of a material capable of allowing transmission of electromagnetic radiation of sufficient intensity to enable performance of an optical measurement (e.g., the material is a semi-transparent or a transparent material). In one embodiment, at least the optical window is comprised of a semi-transparent or a transparent material. The material is also capable of maintaining a liquid sample within the measurement area of the device by capillary action.

In one embodiment, the invention provides an adaptor 190 (FIG. 2*a*) that can be used to connect the body to a pipette, (a pipette as used herein, unless otherwise specified, refers to that aspiration causing portion of a pipette e.g., such as a Pipetman®, a Gilson®, Rainin®, Eppendorf® or Finnipipette® pipette, also referred to as pipettor), a fluid-delivery device or to an interface to such a device (e.g., to a pipette tip). In one aspect, the adaptor comprises a first opening and a second opening and walls defining a lumen through which a fluid (liquid or air may pass). In another aspect, the first opening is dimensioned to receive a portion of the apparatus body while a second opening is dimensioned to receive an end of a pipette, a pipettor, a fluid-delivery device or to an interface to such a device. In a further aspect, the first opening is polygonal (e.g., square or rectangular) while the second opening is round or elliptical or oval. The lumen may comprise a varying internal diameter for at least part of its length to further conform to the dimensions of a tapering end of a pipette.

Figure 2A:
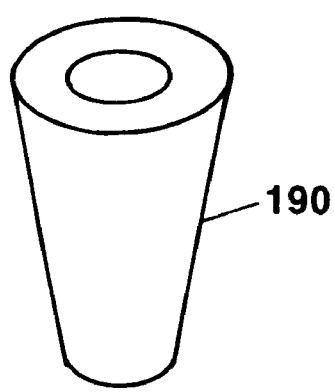
Figure 2B:
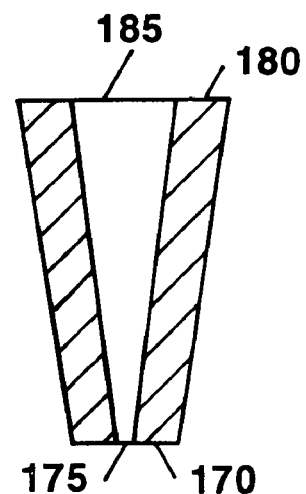

An example of such an adaptor for use with a pipette is shown in FIGS. 2*a*-2*c*. In operation, a pipette may be used for aspirating the sample into the body 110. FIGS. 2*a*-2*c* show an embodiment 190 of the adaptor with one end 170 having an opening 175 capable of providing a substantially gastight connection to one end of the body (110, FIG. 1*c*) and another end 180 having an opening 185 capable of connecting to a conventional pipette (e.g., such as a Pipetman®, a Gilson®, Rainin®, Eppendorf® or Finnipipette® pipette, also referred to as pipettor). In one embodiment, the adaptor comprises a pipette tip that forms a substantially gas-tight connection with a body 110 configured, e.g., as shown in FIGS. 1*a*, 1*b* and 1*c*. The adaptor can be made any suitable material because it will generally not contact liquid sample and will not be in light path.

FIGS. 3*a*-3*e* show another embodiment 210 of an apparatus of this invention in which a body 210 comprises at least two sections. In this embodiment, the body 210 has two ends 220, 230, each end having an opening 295, 250. The first end 220 with opening 295 is capable of connecting to a conventional pipette for aspiration and dispensing, while the second end 230 with opening 250 is capable of being dipped into a liquid well for aspirating liquid. In one embodiment, the body 210 also has two passageways, shown in the Figure as flow channel sections 240 and 260, each having different dimensions. Both of the flow channel sections 240, 260 have parallel inner and outer surfaces which are substantially planar, forming a flow channel 250, 270, with different dimensions $L_1$ and $L_2$ flow channel length $H_1$ and $H_2$, and flow width (aperture width) $W_1$ and $W_2$. In one aspect, the flow channels are rectangular. In another aspect, at least one of the flow channels has an aspect ratio less than 1.

In one aspect, the two flow channels are joined by a taper transition area 280, that has internal rectangular flow channel. In one embodiment, the upper section 210, which includes the first end 220 with opening 295, generally has a round taper shape 295 in order to fit a conventional pipette. In one aspect, the openings 250 are co-centered and the flow channels share the same longitudinal axis. In another aspect, at least one of the flow channels comprises dimensions that are suitable for holding a liquid sample within the flow channel by capillary action.

In the embodiment shown in FIGS. 3*a*-3*e*, the two planar flow sections 240 and 260 are designed to minimize sample volume. An of flow channel 240 is a channel with dimensions $0.2 \text{ mm}(L_1) \times 4 \text{ mm}(H_1) \times 2 \text{ mm}(W_1)$, to produce a 1.6 µl channel volume. Another example of a flow channel 260 is a channel with dimensions of $0.5 \text{ mm}(L_2) \times 3 \text{ mm}(H_2) \times 3 \text{ mm}(W_2)$ to provide a 4.5 µl channel volume. The total volume of two channels 250 and 270 including the transition section is less than 8 µl.

The dimensions of sections of the body may vary and are not limiting features of the invention. However, in certain aspects, $L_1$ ranges from about 0.05 to about 5 mm, $L_2$ ranges from about 0.05 to about 10 mm, $H_1$ ranges from about 0.25 to about 50 mm, $H_2$ ranges from about 0.25 to about 50 mm, $W_1$ ranges from about 0.25 to 25 mm, and $W_2$ ranges from about 0.25 to about 25 mm.

In one aspect, flow channel 150 (FIG. 1*c*) or two flow channel sections 240 and 260 (FIG. 3*a*) define an optical path comprising a substantially predetermined pathlength for transmission of electromagnetic radiation.

In another embodiment, shown in FIGS. 4*a*, 4*b* and 4*c*, the invention further provides a holder comprising a housing 310 capable of receiving a body 110 or 210 and of holding the body (110 or 210). The housing shown in FIG. 4 has two co-axial side openings 325, 335 with an axis of each of the openings perpendicular to the housing axis, the two openings being substantially aligned. In one aspect, the center of the optical window of the body is co-centered with the axes of the openings and the surface of an optical window is perpendicular to excitation light from a source light in an instrument in which the apparatus of this invention is used (e.g., such as a spectrophotomer). The openings 325, 335 and the body 110 define a transmission path for electromagnetic radiation when the body 110 is held in the housing 310 and are adapted to receive electromagnetic radiation. Since when the body 110 is held in the housing 310, the center of the optical window of the body is co-centered with the axes of the openings and the planar surface of the optical window is substantially perpendicular to the longitudinal axis of a beam of excitation electromagnetic radiation, the housing 310 does not require focusing optics.

In another embodiment, the openings 325, 335 are capable of receiving portions (e.g., such as ends) of optical waveguides such as fiber optic connectors. In that embodiment, which is shown in FIG. 4*a*, both source-side and detection-side optical fibers 320 and 330, respectively, are provided.

The center of the optical window of the body may be co-centered with the axes of a collimated source of electromagnetic radiation or with the longitudinal axes of optical waveguides. For example, a planar square surface of an optical window may be provided which is perpendicular to excitation light from a light source. The bottom face of the housing is not necessary closed, but in one aspect, a closed bottom reduces the stray light (e.g., non-source light) getting into the sample pathlength in order to improve the sensitivity of optical measurement. In certain aspects, an adaptor 340 may be used to interface the top face of the housing with the body of the apparatus to reduce stray light.

In one embodiment, the housing 310 can seat the body 110 (or at least a measurement area of the body) at a position that aligns the optical window of the body 110 with a light path defined by source-side and detection side optical fibers, such that sufficient light from the source-side fiber passes through the window to the detection-side optical fiber to be detected by a detector and distinguished from background signal (e.g., produced by a blank).

In certain embodiments in which a body 210 comprises at least two optical windows, the housing 310 can seat the body 210 at two positions (shown by double arrow line in FIG. 4*c*) to align one of the two optical windows to the openings at each position. The apparatus may be positioned within the housing by manually pressing frictional or mechanical detents or by providing an automatic and/or motor-assisted element that can move in an appropriate direction (e.g., see, 360 in FIG. 4*a*), for example. Such frictional or mechanical detents and/or motor-assisted elements comprise exemplary representations of a securing component. The securing component positions the measurement region including at least one optical window in order to provide a transmission path.

In one aspect, during operation, the apparatus of this invention is fitted to a conventional pipette (a pipette or pipettor, as used herein, unless otherwise specified, refers to that aspiration-causing portion of a pipette or pipettor, such as a Pipetman®, a Gilson®, Rainin®, Eppendorf® or Finnipipette® pipette) by a substantially gas-tight fitting, either directly, as in embodiment 210, or indirectly, e.g., using an adaptor 190.

In one aspect, the pipette/pipettor is used to aspirate a liquid sample, for example, a biological sample comprising a biopolymer such as a nucleic acid, peptide, polypeptide and/or protein, into the body (110 or 210) of the apparatus. After a sufficient amount of sample (e.g., 1-2 μl) is aspirated into the body (110 or 210) to fill a measurement area (e.g., such as an entire optical window channel region), the body is placed into a housing 310, as shown in FIGS. 4*a*, 4*c*. The body can be moved in an axial direction in the housing 310 to provide one more predetermined pathlength measurements. In one aspect, due to the dimensions of the passage defined by the inner walls of the body, capillary force will hold the liquid sample in the measurement area. Both vertical placement of the tip and capillary force may be used to substantially eliminate the likelihood of air bubbles being generated. After completion of optical measurement, the body (110 or 210) may be pulled out of the housing and discarded.

Figure 5:
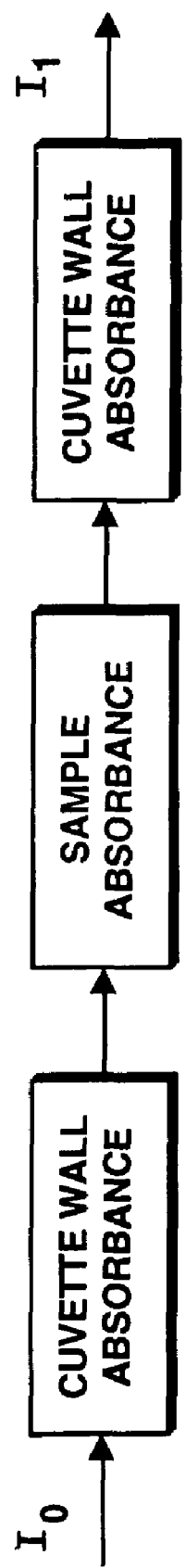
FIG. 5 is a block diagram illustrating the light absorbance in the pathlength defined by an apparatus of the invention in a holder housing.

FIG. 5 illustrates the measurement of an optical property of a sample held in the measurement area of an apparatus according to the invention. Referring to FIG. 5, the total signal ($A_{total}$) (e.g., such as absorbance) would be $$A_{total} = 2A_{body\ wall} + A_{sample} > A_{sample}$$

Where $2A_{body\ wall}$ refers to the signal contributed by a first and second parallel walls of the apparatus body which define the measurement area (each wall comprising an inner and outer side) and $A_{sample}$ refers to the signal contributed by a sample held between the walls by capillary action.

Since a blank measurement is generally required before the sample measurement, the actual measurement reading would still be $A_{sample}$ (i.e., the signal from the body walls would be subtracted). Hence, the optical signal produced by a wall of the apparatus will not affect the measurement of an optical signal from the sample.

The invention also provides methods for detecting, monitoring (e.g., determining a change in) and/or quantitating an optical property of a sample.

In one aspect, the method comprises placing the measurement area of an apparatus according to the invention in a positional relationship to a light source and detector of an optical detection device (e.g., a spectrophotometer, photometer, spectrofluorometer, and the like) such that a light path is provided from the light source through the measurement area, to the optical detection device. In certain aspects, the light path is at least partially defined by an optical waveguide, for example a source-side optical fiber and/or a detection-side optical fiber. In certain other aspects, other optical elements may be used to further define the light path. In one aspect, a sample, such as a liquid sample, is held in the measurement area by capillary force and the detector detects, monitors and/or quantitatively identifies an optical property of the sample (e.g., such as absorption, emission, or scattering of light). In one aspect, the concentration of a component (e.g., a nucleic acid, polypeptide, peptide, or protein) in a sample can be determined by comparing light transmission by a sample without the component to light transmission by a sample with the component. A standard curve may be used in certain cases to correlate optical properties (e.g., such as absorbance) with characteristics of the sample (e.g., such as concentration of a biomolecule within the sample).

In one embodiment, a liquid sample is placed within the measurement area of the apparatus by interfacing the apparatus body with a pipette or pipettor, either directly or indirectly using an adaptor as described above, and aspirating a sample from a sample source into the measurement area. In certain aspects, the apparatus may be placed into a sample holder-receiving area of an optical device (such as a spectrophotometer) or into a cartridge for receiving such a sample holder, which may be placed in the device. In one aspect, the ejector of a pipette/pipettor can be used to place the apparatus into the sample holder-receiving area or cartridge.

Although embodiments of the invention have been described with respect to applications to specific liquid samples (analytes) and specific optical equipment, it should be noted that these are not limitations of this invention and are only presented for exemplary purposes.

Although the invention has been described with respect to various embodiments, it should be realized this invention is also capable of a wide variety of further and other embodiments within the spirit and scope of the appended claims.

What is claimed is:

1. An apparatus comprising:
   a body comprising:
   a first opening located at a first end;
   a second opening located at a second end;
   two planar inner surfaces, and two planar outer surfaces, said two planar outer surfaces being substantially parallel to said two planar inner surfaces;

at least a portion of at least one inner surface and its corresponding outer surface being at least partially transparent;

an inner space of said body connecting said first opening and said second opening, providing a passage from said first opening to said second opening; and said two planar inner surfaces forming two planar and parallel sides of at least a portion of said passage, said portion of said passage being dimensioned to hold a liquid sample within said portion of the passage by capillary action and forming a measurement region with a predetermined optical pathlength.

2. The apparatus of claim 1 further comprising:
a hollow adaptor body comprising:
  a first opening at a first adaptor body end, and
  a second opening at a second adaptor body end,
  said second opening of said hollow adaptor body being capable of providing a substantially gastight connection to said first end of said body,
  said first adaptor body end and said first opening of said adaptor body being capable of operatively connecting to a pipette/pipettor.

3. The apparatus of claim 1 wherein said body comprises at least two sections;
wherein one of said at least two sections comprises said first opening and said first end; and,
wherein said first end is capable of operatively connecting to a pipette/pipettor.

4. The apparatus of claim 3 wherein said at least two sections comprise at least three sections; and
at least one other of said at least three sections comprises said two planar inner surfaces and said two planar outer surfaces.

5. The apparatus of claim 1 further comprising:
an outer coating layer disposed over a portion of an outer surface of said body.

6. The apparatus of claim 5 wherein at least a portion of said outer surfaces is not covered by said outer coating layer.

7. The apparatus of claim 6 wherein an outer surface of said body is at least partially coated with or comprises a hydrophobic material.

8. The apparatus of claim 1 further comprising:
a housing receiving said body;
said housing comprising:
  a first housing opening, and a second housing opening,
  said first housing opening and said second housing opening being substantially aligned;
  said first housing opening, said second housing opening and said measurement area of said body constituting a transmission path for electromagnetic radiation when said body is held in said housing.

9. The apparatus of claim 8 wherein said first housing opening and/or said second housing opening are capable of being in optical communication with an optical fiber.

10. The apparatus of claim 1 wherein said measurement area is capable of holding a liquid sample volume of no more than about 10 µl.

11. The apparatus of claim 1 wherein said measurement area is capable of holding a liquid sample volume of no more than about 5 µl.

12. The apparatus of claim 1 wherein said measurement area is capable of holding a liquid sample volume of no more than about 2 µl.

13. The apparatus of claim 1 wherein said predetermined path length is no more than about 2 mm.

14. The apparatus of claim 1 wherein said predetermined path length is no more than about 1 mm.

15. An apparatus of claim 1, wherein said passage comprises a first section and a second section and wherein the dimensions of a cross-section through said first and second section are different.

16. The apparatus of claim 1 further comprising:
a housing capable of receiving said body;
said housing comprising:
  a first housing opening, and a second housing opening;
  the centers of said first housing opening and said second housing opening being substantially aligned;
  said first housing opening, said second housing opening and said measurement area of said body providing a transmission path for electromagnetic radiation when said body is held in said housing; and
  a securing component interior of said housing, said securing component being capable of securing said body in at least one predetermined position.

17. The housing of claim 16, wherein the first housing opening is capable of being connected to an end of a source-side optical fiber and the second housing opening is capable of being connected to detection-side optical fiber of an optical detection device.

18. The housing of claim 16 wherein said at least one predetermined position comprises two predetermined positions.

19. A method for measuring an optical property of a liquid sample, comprising the steps of:
providing an apparatus having a body comprising:
  a first opening located at a first end;
  a second opening located at a second end;
  two planar inner surfaces, and
    two planar outer surfaces, said two planar outer surfaces being substantially parallel to said two planar inner surfaces;
  at least a portion of at least one inner surface and its corresponding outer surface being at least partially transparent;
  an inner space of said body connecting said first opening and said second opening, providing a passage from said first opening to said second opening; and
  said two planar inner surfaces forming two planar and parallel sides of at least a portion of said passage, said portion of said passage being dimensioned to hold a liquid sample within said portion of the passage by capillary action and forming a measurement region with a predetermined optical pathlength;
placing the measurement area of the apparatus in a positional relationship to a light source and detector of an optical detection device such that a light path is provided from the light source through the measurement area, to the optical detection device, wherein the measurement area of the apparatus holds the liquid sample.

20. The method of claim 19, wherein a sample is placed in the apparatus by interfacing the apparatus with a pipette/pipettor and aspirating the liquid sample into the measurement area.

21. The method of claim 19, wherein, a liquid sample is placed in the measurement area by contacting an end of the apparatus to a liquid sample and allowing the sample to flow into the measurement area by capillary action.

22. The method of claim 19, wherein the optical detection device is a spectrophotometer.

23. The method of claim 19, wherein the liquid sample comprises a nucleic acid.

24. The method of claim 18, wherein the liquid sample comprises peptides, polypeptides, or proteins.

25. The method of claim 18, wherein the optical property is light absorbance.

26. The method of claim 24, wherein the optical property is correlated with a concentration of a biomolecule in the sample.

* * * * *